United States Patent
Belly et al.

(10) Patent No.: US 6,469,159 B1
(45) Date of Patent: *Oct. 22, 2002

(54) METHODS FOR EXTRACTING NUCLEIC ACIDS FROM TISSUE SAMPLES AND PARAFFIN-EMBEDDED TISSUES

(76) Inventors: Robert T. Belly, 1144 Ohstrom Park, Webster, NY (US) 14580; Gary J. Chilson, P.O. Box 64, Elba, NY (US) 14058

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/301,374

(22) Filed: Apr. 26, 1999

(51) Int. Cl.[7] ............................ C07H 21/00; C07H 1/06
(52) U.S. Cl. ........................ 536/25.4; 435/6; 435/91.1; 435/91.2; 435/810; 435/40.5
(58) Field of Search .............................. 536/25.4; 435/6, 435/91.1, 91.2, 810, 40.5

(56) References Cited

U.S. PATENT DOCUMENTS

| | | |
|---|---|---|
| 4,900,677 A | 2/1990 | Hewitt |
| 5,231,015 A | 7/1993 | Cummins et al. |

FOREIGN PATENT DOCUMENTS

| | | |
|---|---|---|
| EP | 0 393 744 A1 | 10/1990 |
| EP | 0 428 197 A2 | 5/1991 |
| NZ | 233270 | 4/1990 |
| WO | 95/05461 A1 | 2/1995 |
| WO | 96/32500 | 4/1995 |

OTHER PUBLICATIONS

Almoguera et al, Cell, 53:549–554, 1998.
Banergee et al, Bio. Techniques, 18:768:773, 1995.
Bos, J. L., Cancer Research, 49:4682–4689, 1989.
Crisan and Mattson, DNA and Cell Biology, 12:455–464, 1993.
Crisan et al, Clin Biochem, 25:99–103, 1992.
Greer et al, Am. J. Clin. Pathol., 95:117–124, 1991.
Peek, K. et al, Eur. J. Biochem, 207:1035–1044, 1992.
Slebos, Diagnostic Molecular Pathology, 1(2):136–141, 1992.
Wilson, I.G., Applied and Evironmental Microbiology, 63(10):3741–3751, 1997.

*Primary Examiner*—James O. Wilson

(57) ABSTRACT

The present invention provides rapid and highly effective methods for extracting nucleic acids suitable for PCR amplification from tissue samples and paraffin-embedded tissue samples. Extraction is accomplished within a few minutes using a composition comprising a buffer, at least one non-ionic surfactant, and a protease enzyme. The sample is then heated at alkaline pH and after a centrifugation step, the DNA is the supernatant can be used directly in known amplification methods, such as PCR.

15 Claims, No Drawings

METHODS FOR EXTRACTING NUCLEIC ACIDS FROM TISSUE SAMPLES AND PARAFFIN-EMBEDDED TISSUES

BACKGROUND OF THE INVENTION

1. Field of the Invention

The present invention relates to methods and kits for the extraction of nucleic acids. In particular, the present invention relates to methods for extracting nucleic acids from tissue samples and paraffin-embedded tissue samples.

2. Background Information

Within the field of biological diagnostics, molecular-based techniques involving the amplification of nucleic acids are being used increasingly for the detection of inherited diseases, cancer, and infectious diseases. However, in applying such amplification techniques with tissues or other important clinical samples, impurities in nucleic acid preparations can inhibit or reduce the sensitivity and efficiency of amplification (Wilson, I. G., Applied and Environmental Microbiology 63(10):3741–3751, 1997).

DNA extraction from archival paraffin-embedded pathology tissue samples is particularly useful in retrospective studies in which the determination of a molecular diagnosis can be correlated with patient outcome. As pointed out by Crisan and Mattson (DNA and Cell Biology 12:455–464, 1993), the advantages of retrospective DNA analysis are multiple and can be applied to: (i) the study of numerous disease processes, where viral, bacterial, or parasitic agents are suspected to play an etiologic role becomes possible and epidemiological or prognostic correlation may be derived; (ii) the study of endogenous DNA abnormalities associated with various types of malignancies; (iii) the study of inherited DNA in genetic diseases; (iv) retrospective studies of rare diseases for which use of archival specimens would allow larger patient study groups than would be possible in prospective studies requiring fresh tissues; and (v),the possibility of correlating the presence or absence of a particular disease, morphological diagnosis or type, disease stage, prognosis, and response to treatment, where the clinical outcome is already known.

Methods reported for the amplification of DNA are based either on the use of a DNA polymerase (e.g., polymerase chain reaction, PCR), a ligase (ligase chain reaction, LCR), or both (GAP-LCR). Of these methods, PCR has been the most widely used to date. PCR involves the hybridization of primers to the strands of a target nucleic acid in the presence of a DNA polymerization agent and deoxyribonucleoside triphosphates under appropriate conditions. The result is the formation of primer extension products throughout several cycles of amplification, and exponential multiplication of the number of original target sequences. Further details about PCR can be obtained by consulting U.S. Pat. No. 4,683,195 (Mullis, et al), U.S. Pat. No. 4,683,202 (Mullis), and U.S. Pat. No. 4,965,188 (Mullis et al).

Because of its inherent sensitivity, product carryover and contamination between samples is a problem with PCR and nucleic acid based amplification systems in general. Product carryover during sample preparation is a serious problem. It is a function of the amount of time that a sample is exposed to the external environment, and related to the number of times the sample containment device must be opened, thereby exposing the sample to the external environment. Thus, it is advantageous to have a sample preparation method that is rapid and allows reduced or minimal exposure of the sample to the external environment; particularly, it is an advantage to provide a method of nucleic acid extraction where the number of times the sample containment device has to be opened is minimal.

Point mutations in the ras proto-oncogenes occur with great frequency in many human cancers, and are a potentially important diagnostic target (Bos, J. L., Cancer Res. 49:4682–4689, 1989). For example, as much as 90% of pancreatic cancer involves a mutation in the K-ras gene; the majority occurring in codon 12 (Almoguera et al., Cell 53:549–554, 1998). There are a number of methods for detecting the presence of a ras mutation. One method, restriction endonuclease mediated selective-PCR (REMS-PCR) has been described recently (WO 9632500). REMS-PCR is based upon the use of a thermostable restriction enzyme during PCR thermocycling. REMS-PCR greatly simplifies and decreases the time required for analysis and detection.

As pointed out by Volenandt et al., the amount of extracted DNA can dramatically affect the yield in a PCR reaction (Polymerase Chain Reaction Analysis of DNA from Paraffin-Embedded Tissue. Methods in *Molecular Bioloqy Vol. 15: Current Methods and Applications*, 1993, edited by: B. A. White, Humana Press Inc., N.J.) When analyzing DNA from fixed tissue, an inverse relationship between the volume of extracted sample added and PCR amplification yield often is observed. This is due to the effects of certain fixatives and other inhibitors on Taq DNA polymerase activity. Furthermore, nucleic acid fragmentation occurring during fixation or DNA extraction also can be a problem in amplification of DNA (Greer et al., Am. J. Clin. Pathol. 95:117–124, 1991; and Crisan et al., Clin. Biochem. 25:99–103, 1992).

In the case of DNA extraction from paraffin or fresh tissue sections, complex methods for DNA preparation are typically used. Such methods require long incubations with protease enzymes in the presence of surfactants to release DNA and to degrade proteins that can interfere in nucleic acid amplification. Other subsequent steps in purification of extracted DNA may include treatment with an RNAase to remove contaminating RNA, followed by DNA precipitation with a solvent such as ethanol or a mixture of solvents such as phenol and isoamyl alcohol to remove protein and other cellular material, followed by DNA hydration (Volenandt et al., Polymerase Chain Reaction Analysis of DNA from Paraffin-Embedded Tissue. Methods in *Molecular Biology Vol. 15: Current Methods and Applications*, 1993, edited by: B. A. White, Humana Press Inc., N.J.). In the case of paraffin-embedded tissues, paraffin is usually removed by extraction with solvents such as xylene in a multiple step procedure prior to the proteinase step. A recent report by Banerjee et al. provides a protocol for DNA release from paraffin-embedded tissues (BioTechniques 18:768–773, 1995). The method involves the following steps: (1) microwave treatment, (2) removal of the paraffin by a centrifugation step, (3) Proteinase K digestion, and (4) a heat step to destroy Protease K activity.

Slebos and his associates have reported a method for releasing DNA from paraffin-embedded tissue which includes the use of three 10 micron sections, an incubation with a non-ionic detergent, and an 18–24 hr incubation with Proteinase K, followed by centrifugation (Diagnostic Molecular Pathology 1(2):136–141, 1992). The resultant supernatant is used directly in PCR amplification.

To overcome the need for long incubation with Proteinase K and the need for a heat inactivation step, the provisional specification of NZ 233270 describes the use of a thermostable proteinase instead of Proteinase K for digestion of cell protein and release of nucleic acid. This method provides an improvement in speed and ease-of-use. However, it is limited by the amount of amplifiable DNA that is released from paraffin-embedded tissue. Thus, there is still a need in the art for a rapid and highly effective means of extracting nucleic acids from tissue samples in a manner that is compatible with subsequent amplification procedures.

SUMMARY OF THE INVENTION

The present invention overcomes the above-noted problems and provides a needed means of extracting nucleic acids from tissue samples in a manner compatible with subsequent amplification methods. Thus, it is an object of the present invention to provide methods and kits for extracting nucleic acids from tissue samples and paraffin-embedded tissue samples.

Various other objects and advantages of the present invention will be apparent from the detailed description of the invention.

In one embodiment, the present invention relates to a method of extracting nucleic acids from tissue samples. The method comprises contacting the tissue sample with a buffer, at least one nonionic surfactant, and a protease enzyme under conditions sufficient to releases the nucleic acids from the sample. The sample is then heated at an alkaline pH for a period of time sufficient to inactivate the protease enzyme. By centrifuging the sample, the nucleic acids are isolated in the supernatant.

All publications mentioned herein are hereby incorporated by reference.

DETAILED DESCRIPTION OF THE INVENTION

The present invention relates to methods for extracting nucleic acids from tissue samples so that the extracted nucleic acids are suitable for subsequent amplification and detection using known techniques. Using the present invention, nucleic acids (DNA and/or RNA) can be extracted from human tissue samples, both fresh tissue samples and paraffin-embedded tissue samples. Examples of tissues from which nucleic acids can be extracted using the present invention include, but are not limited to, both normal and cancerous lung tissue, colon tissue, pancreatic tissue, breast tissue, prostate tissue, blood and other body fluids or cellular material containing nucleic acids that can be detected.

In the present invention, tissue samples suspected of containing DNA of interest are contacted with a buffer, at least one nonionic surfactant, and a protease enzyme; sequentially or simultaneously. Suitable common biological buffers include one or more organic buffers that maintain the pH at from about 4 to about 10, and preferably at from about 7 to about 9. Useful buffers include, but are not limited to, 3-(N-morpholino)propanesulfonic acid, 3-(N-morpholino) ethanesulfonic acid, tricine, glycine, TRIS, phosphate, and others readily apparent to those skilled in the art. The amount of buffer used is dependent upon the pKa and is that sufficient to maintain the desired pH.

Any of number of nonionic surfactants can be utilized in the present invention. Examples of surfactants useful in the present invention include, but are not limited to, polyoxyethylenesorbitan derivatives, polyoxyethylene ethers, polyglycol ethers, perfluoroalkyl polyoxyethylenes, fluorinated alkyl alkoxylates and fluorinated alkyl ester compounds. Other useful classes of surfactants and examples of each class would be readily apparent to one skilled in the art, especially after consulting the standard reference for surfactants, McCutcheon's Emulsfers and Detergents, 1986 North American Edition, McCutcheon Division Publishing Co., Glen Rock, N.J. Representative nonionic surfactants are also provided in U.S. Pat. No. 5,231,015 (Cummins et al.), the contents of which are hereby incorporated by reference. Combinations of nonionic surfactants can also be used in the present invention.

Protease enzyme is used to break down tissues and protein helping to release the nucleic acids. The protease may also degrade nucleases making the released DNA more stable. Preferably, the protease enzyme is thermostable. A wide variety of proteases can be used in the present invention including serine proteases (E. C. 3.4.21, e.g. Typsin, and chymotrypsin), Thiol proteases (E. C. 2.4.22, e.g., papain, ficin), carboxy (acid proteases, E. C. 2.4.23, e.g., pepsin), and metalloproteases (E. C. 2.4.24, e.g.,thermolysin, pronase). Optimum conditions of temperature, pH, ionic strength, and surfactant type may differ depending upon the protease used. Preferred proteinases include Protease K (E. C. 3.4.21.64 from Tritirachium album), protease from Streptomyces griseus (P6911, Sigma Chemical Company, St. Louis), and PRETAQ. PRETAQ is a very thermostable alkaline protease isolated from Thermus sp. Strain RT41 as described by Peek, K., et al. (Purification and characterization of a thermostable proteinase, Eur. J. Biochem 207:1035–1044, 1992). The enzyme is extremely thermostable with no loss of activity reported after 24 hr at 70° C., and no loss of activity at room temperature over 6 months. The use of PRETAQ and similar thermostable enzymes have advantages in the preparation of DNA from paraffin tissues since paraffin melts at temperatures around 75° C. and above. Thus, the use of such highly thermal stable proteases eliminates the need for separate solvent based extraction protocols for paraffin removal prior to protease digestion. Solvent based de-paraffinization procedures are described in references by Volkenandt et al, Wright and Manos, and Greer, as cited previously, and are based on the use of multiple step treatments with octane or xylene followed by treatment with ethanol or other alcohols, or solvents such as acetone.

The sample is contacted with the buffer, nonionic surfactant and protease enzyme under conditions sufficient to release the DNA. The conditions employed will vary depending on the tissue sample and the protease used but are readily determinable by those skilled in the art. For example, when using PRETAQ protease, the sample can be contacted with the buffer, nonionic surfactant and protease at 70° C. to 100° C. for 5 minutes to 3 hours depending upon the temperature. At 90° C. to 100° C., 10–15 minutes is preferred. If Protease K is utilized, the sample can be contacted with the buffer, nonionic surfactant and protease for 30 minutes to 24 hours. Preferably, for 30 minutes to 60 minutes.

The sample is then heated at an alkaline pH for a period of time sufficient to inactivate the protease. The pH of the sample can be adjusted by adding sodium hydroxide or potassium hydroxide to the sample until an alkaline pH is achieved. The extracted nucleic acids can then be isolated by centrifugation.

The method disclosed in the present invention has many advantages. The method is rapid, eliminates the need for potentially toxic solvents, and minimizes the number of manipulations in which the sample containment device has to be opened. The inclusion of a treatment step with heated alkali improves PCR amplification, probably by denaturing the double stranded DNA and converting it into smaller pieces of single-stranded DNA which are more readily amplifiable in PCR. Treatment with hot alkali also is expected to denature the protease, eliminating the concern that residual protease activity would inhibit TAQ polymerase or other enzymes required for subsequent amplification. Thirdly, it is also expected that several chemical agents (heparin, bilirubin, hemoglobin etc.) known to inhibit PCR amplification are denatured by hot alkali treatment. Fourthly, hot alkali treatment destroys RNA which may be an interferent in some amplification protocols. Finally, hot alkali treatment also would be expected to result in solubilization of lipids, fatty acids and other crucial cell membrane. This disruption of the integrity of the cell membrane also would be expected to increase DNA released from cells and tissues.

Nucleic acids extracted from tissue samples according to the present invention are suitable for subsequent amplification using known methods in the art such as PCR and LCR. The general principles and conditions for amplification and detection of nucleic acids using PCR are quite well known, the details of which are provided in numerous references, including U.S. Pat. No. 4,683,195 (Mullis et al.), U.S. Pat. No. 4,683,202 (Mullis), and U.S. Pat. No. 4,965,188 (Mullis et al.), all of which are incorporated herein by reference. Preferably, PCR is carried out using a thermostable DNA polymerase. A number of suitable thermostable DNA polymerases have been reported in the art, including those mentioned in detail in U.S. Pat. No. 4,965,188 (Gelfand et al.) and U.S. Pat. No. 4,889,818 (Gelfand et al.), both incorporated herein by reference. Other reagents that can be used in PCR include, for example, antibodies specific for the thermostable DNA polymerase, which inhibit the polymerase prior to amplification. Such antibodies are represented by the monoclonal antibodies described in U.S. Pat. No. 5,338,671 (Scalice et al.), the contents of which are hereby incorporated by reference.

Amplified nucleic acids can be detected in a number of known ways, such as those described in U.S. Pat. No. 4,965,188 (Gelfand et al.). For example, the amplified nucleic acids can be detected using Southern blotting, dot blot techniques, or nonisotopic oligonucleotide capture detection with a labeled probe. Alternatively, amplification can be carried out using primers that are appropriately labeled, and the amplified primer extension products can be detected using procedures and equipment for detection of the label. Thus, in view of the teachings in the art and the specific teachings provided herein, a worker skilledsin the art should have no difficulty in practicing the present invention to extract nucleic acids from fresh tissue or paraffin-embedded tissue samples, which are suitable for subsequent PCR amplification and detection.

As used herein, when in reference to time the term "about" refers to +/−10% of that time limit. When used in reference to temperatures, the term "about" refers to +/−5° C.

The following Examples are provided to illustrate certain embodiments of the present invention, and are not to be construed as limiting the invention.

EXAMPLES

Material and Methods

Paraffin-embedded Tissues

For the analysis of paraffin-embedded tissues, a 10-micron section was cut from a paraffin block, and placed in a sterilized 1.5 mL screw cap tube. To prevent contamination between samples, a new blade was used with each new paraffin block. The blade and microtome area were cleaned with a jet of compressed air after each section was cut. A fresh wooden applicator stick was used to transfer each section into its containment tube.

Restriction Endonuclease Mediated Selective PCR (REMS-PCR) Mutational Analysis

Mutations at the first and second bases of codon 12 of the K-ras gene were detected using REMS-PCR. Each PCR reaction contained three sets of primers (Table 1). The diagnostic primers induce a Bstn-1 restriction site in the wild-type ras, but not in a mutation at codon 12. Thus, ras wild-type DNA is selectively cleaved during PCR thermocycling, and mutant sequences of ras at codon 12 are enriched. The PCR control primers verify that PCR amplifiable DNA is extracted, and the enzyme control primers verify that the restriction enzyme is functioning.

TABLE 1

REMS-PCR Primer Sequences for K-ras codon 12

| Primer | Sequence |
| --- | --- |
| 5BKIT (Diagnostic) (biotinylated) | TATAAACTTG TGGTAGTTGG ACCT (SEQ. ID NO. 1) |
| 3K2 (Diagnostic) | CGTCCACAAA ATGATTCTGA (SEQ. ID NO. 2) |
| 5BK5 (PCR control) (biotinylated) | TCAGCAAAGA CAAGACAGCT A (SEQ. ID NO. 3) |
| 3K6 (PCR control) | AGCAATGCCC TCTCAAGA (SEQ. ID NO. 4) |
| 5BK28 (Enzyme control) (biotinylated) | AGTAAAAGGT GCACTGTA ATAATC (SEQ. ID NO. 5) |
| 3K29 (Enzyme control) | GTGTCGAGAA TATCCAAG AGCCA (SEQ. ID NO. 6) |

For REMS-PCR, reaction mixtures contained 12 units/100 μL of recombinant Taq polymerase, 0.842 μL of Taq inhibiting antibody TP4-9.2 (a 5 fold excess), 10 mM HT50 buffer (100 mM NaCl, and 50 mM Tris.HCl, pH 8.3), 0.3 μM of primer 5BKIT and 3K2, and 0.05 μM of primers 5BK5, 3K6, 5BK28, and 3K29, 0.2 mM total dinucleoside triphosphates (dNTPs), 0.6 units/μL of Bstn1 (New England BioLabs, Beverly Mass.), 1 mM dithiothreitol (DTT), 4 mM MgCl2, sample (typically 3 μL) and deionized water up to a final volume of 100 μL. Typically, the Taq and anti-Taq antibodies were mixed and incubated for 10–15 minutes prior to the addition of the other PCR reaction components. Bstn1 restriction enzyme was added last to the reaction mix just before the addition of sample.

The above reaction mixture was amplified and detected using an Ortho-Clinical Diagnostics, Inc. pouch containment system for nucleic acid amplification and detection as described in U.S. Pat. No. 5,089,233, U.S. Pat. No. 5,229,297, and U.S. Pat. No. 5,380,489. Briefly, sample plus PCR reagents, as described above, were mixed and loaded into a blister of the pouch, and the pouch was sealed. Biotin-labeled diagnostic, PCR control, and enzyme control primers were used in amplification. The "PCR Reaction Blister" was heated at 94° C. for 1 min, followed by 30 amplification cycles, each cycle having a melt temperature of 94° C. and a 10 second incubation, followed by annealing for 75 seconds at 58° C. After a postheat incubation for 5 min at 103° C., the amplified product was detected after the reaction products were forced through a detection chamber where they hybridized with complementary oligos attached to beads (Table 2). The horseradish peroxidase (HRP) channel, and the wash channel were at 55° C., whereas, a temperature of 40° C. was used in the detection channel. The hybridized product was detected after HRP-streptavidin and subsequently the HRP-dye substrate was forced through the detection chamber.

TABLE 2

Capture Oligo Sequences

| Capture Oligo | Sequence |
|---|---|
| Cap-2E | 5' GACTGTGTTT CTCCCTTCTC AGGATTCC (SEQ. ID NO. 7) |
| K-CapD8 | 5' TATCGTCAAG GCACTCTTGC CTACGCCA (SEQ. ID NO. 8) |
| K-Cap6 | 5' GACATAACAG TTATGATTTT GCAGAAAA CAGATC (SEQ. ID NO. 9) |
| INC 26.7 | 5' TTAGTAGTAG AAGGACGACG ATGGCG (SEQ. ID NO. 10) |

At the 3' end of each oligonucleotide in Table 2, a linker of the following sequence was used for attachment to polystyrene beads, 557T, where base #5 is a tetraethylene glycol (TEG)spacer and Base #7 is an Aminodiol linker (AD linker), and T is a thymidine sequence.

Each pouch contained 3 detection blisters, each with 200 μL of fluid (streptavidin HRP 200 μL/blister; wash 200 μL/blister; and dye/gel 200 μL/blister). The order of blisters was Streptavidin, followed by a wash, and finally a dye/gel blister.

Capture oligo beads were ordered in the pouch (in the direction of flow) as follows: INC 26.7a, K-Cap 6M, No spot, K-capD8, No Spot, K-Cap2E, and INC26.7a.

Example 1

The Extraction of DNA from Paraffin-embedded Tissue in the Presence and Absence of Treatment with NaOH and Heat, after Pre-Tag Treatment.

In this example, 10 micron thick paraffin sections from different cancer samples were extracted as follows: after microtome sectioning, the sectioned sample was placed in a 1.5 mL screw-top microcentrifuge tube. Eighty microliters of TEK buffer (10 mM Tris.HCl buffer, pH 8.0, and 0.5% Tween 20) were added followed by 10 μL of thermostable protease K (Pre-Taq) (0.3 u/μL, Gibco/BRL Products, Gaithersburg, Md.). The tubes were heated at 100° C. for 5 min. One set of duplicate tubes was centrifuged while still hot at 14,000 rpm for 2 min, and the supernatant fluid under the paraffin layer was transferred to a new tube and stored refrigerated at 4° C. prior to analysis. To the second set of duplicate tubes, 10 μL of 250 mM NaOH was added, and the tubes were heated at 105° C. for 3 min in a heat block. While hot, the tubes were centrifuged at 14,000 rpm for 2 min, and the supernatant fluid under the paraffin layer was removed and transferred to a new tube, and stored at 4° C. prior to analysis.

Five microliters of each supernatant were added to a 1 mL cuvette, and DNA concentration was determined on a Beckman model DU70 spectrophotometer by the absorption at 260 nm. The results are provided in Table 3 below.

TABLE 3

Effect of Hot NaOH on DNA extraction from Paraffin-Embedded Tissues after Pre-Taq Treatment

| Tissue (μg/mL) | Treatment | DNA Concentration |
|---|---|---|
| Tonsil | With NaOH | 0.41 |
| Tonsil | No NaOH | 0.20 |
| Colorectal Cancer | With NaOH | 0.28 |
| Colorectal Cancer | Without NaOH | 0.15 |
| Lung Cancer | With NaOH | 0.52 |
| Lung Cancer | Without NaOH | 0.25 |
| Pancreatic Cancer | With NaOH | 0.50 |
| Pancreatic Cancer | Without NaOH | 0.35 |

These studies indicated that for each of the tissues examined there was approximately a 2-fold increase in DNA extracted from the paraffin section when NaOH treatment was used compared with a Pre-TAQ treatment alone.

Four microliters of each supernatant was subjected to PCR amplification for detection of the K-ras mutation of codon 12 based on REMS-PCR in a "pouch assay" as described above. Results of duplicate assays in the pouch system are presented below in Table 4.

TABLE 4

REMS-PCR Pouch analysis of K-12 ras mutations of samples extracted with Pre-Taq in the with and without NaOH treatment

| Sample | NaOH Diagnostic | PCR control | Visual Score Enzyme Control |
|---|---|---|---|
| Pancreatic | + (0,0) | (3,4) | (2,2) |
|  | − (0,0) | (0,1) | (0,1) |
| Colorectal | + (0,0) | (2.5,3.5) | (3,3.5) |
|  | − (0,0) | (2.5,2.0) | (3.5,2.5) |
| Lung | + (0,0) | (2,4) | (1,2.5) |
|  | − (0,0) | (3,2.5) | (1.5,1.5) |
| Tonsil | + (0,0) | (6,6) | (0,0) |
|  | − (0,0) | (6,6) | (0,0) |

The results indicate a significant increase in the K-12 ras diagnostic visual scores for extraction of DNA from pancreatic tissue sections with NaOH treatment, as compared to a control without NaOH treatment. Detectable, although slight, improvements in detection were also observed in the colorectal and lung cancer sections treated with NaOH, as compared to controls. Tonsil sections showed strong amplification (visual score of 6) with or without NaOH treatment.

Example 2

The Extraction of DNA from Paraffin-embedded Tissues with and Without NaOH Treatment, After Treatment with Protease-K In this experiment, four different paraffin-embedded colorectal sections were treated as follows: After microtome sectioning, each section was placed in a 1.5 mL screw-top microfuge tube. Eighty-seven microliters of TEK buffer were added followed by 3 μL of thermostable Protease K (Gentra Systems, Inc. Minneapolis, Minn.). The tubes were incubated at 65° C. for 4 hrs in a heat block. One set of duplicate tubes was placed in a heat block at 100° C. for 5 min, and centrifuged while still hot at 14,000 rpm for 2 min, and the supernatant fluid under the paraffin layer was transferred to a new tube and stored at 4° C. prior to analysis. To a second set of duplicate tubes, 10 μL of 250 mM NaOH was added and the tubes were heated at 105° C. for 3 min in a heat block. While hot, the tubes were centrifuged at 14,000 rpm for 2 min, and the supernatant fluid under the paraffin layer was removed and transferred to a new tube, and stored at 4° C. prior to analysis.

Results of these studies with Protease K treated cells indicate only a slight increase in extracted DNA, determined spectrophotometrically as described above, in samples treated with NaOH as compared to controls (Table 5). However, as shown in Table 6, there was strong amplification with the PCR control primers in samples treated with NaOH and no detectable amplification with the PCR control primers when the NaOH step was omitted.

TABLE 5

Effect of Hot NaOH on DNA extraction from Colorectal Cancer Paraffin Tissues after Protease K Treatment

| Sample (μg/mL) | Treatment | DNA Concentration |
| --- | --- | --- |
| 1 | + NaOH | 1.2,1.2 |
|   | − NaOH | 1.1,1.1 |

TABLE 5-continued

Effect of Hot NaOH on DNA extraction from Colorectal Cancer Paraffin Tissues after Protease K Treatment

| Sample (μg/mL) | Treatment | DNA Concentration |
| --- | --- | --- |
| 2 | + NaOH | 1.3,1.3 |
|   | − NaOH | 1.2,1.2 |

TABLE 6

REMS-PCR Pouch analysis of K-12 ras mutations of samples extracted with Protease-K with and without NaOH treatment

| Sample | Treatment Enzyme Control | PCR control | Visual Score Diagnostic | |
| --- | --- | --- | --- | --- |
| 1 | + NaOH | 4,6 | 0,0 | 0,0 |
|   | − NaOH | 0,0 | 0,0 | 0,0 |
| 2 | + NaOH | 7,7 | 7,6 | 0,0 |
|   | − NaOH | 0,0 | 0,0 | 0,0 |

While the foregoing invention has been described in some detail for purposes of clarity and understanding, it will be clear to one skilled in the art from a reading of this disclosure that various changes in form and detail can be made without departing from the true scope of the invention.

What is claimed is:

1. A method of extracting nucleic acids from tissue samples comprising contacting said sample with a buffer, at least one nonionic surfactant, and a protease enzyme under conditions sufficient to release said nucleic acids from said sample;

adding alkali and heating said sample at an alkaline pH for a period of time sufficient to inactivate said protease enzyme; and centrifuging said sample to isolate said nucleic acids in supernatant.

2. The method of claim 1 wherein the tissue is selected from fresh tissue and paraffin-embedded tissue.

3. The method of claim 1 wherein the nonionic surfactant is selected from the group consisting of polyoxyethylene sorbitan derivatives, polyoxyethylene ethers, polyglycol ethers, perfluoroalkyl polyoxyethylenes, fluorinated alkyl alkoxylates and fluorinated alkyl ester compounds.

4. The method of claim 3 wherein the nonionic surfactant is a polyoxyethylene sorbitan derivative.

5. The method of claim 4 wherein the polyoxyethylene sorbitan derivative is Tween-20.

6. The method of claim 1 wherein the protease enzyme is selected from the group consisting of serine proteases, thiol proteases, carboxy proteases, metalloproteases, Protease K, protease from Streptomyces griseus, and PRETAQ.

7. The method of claim 6 wherein the protease enzyme is a thermostable protease.

8. The method of claim 7 wherein the thermostable protease is PreTAQ.

9. The method of claim 1 wherein the heating step is done at about 70 degrees C to about 100 degrees C for 5 minutes to 3 hours.

10. The method of claim 9 wherein the heating is done at from about 90 degrees C to about 100 degrees C for about 10–15 minutes.

11. A method of extracting nucleic acids from a paraffin-embedded tissue sample comprising the steps of:

(a) contacting said sample with a buffer and a protease enzyme;

(b) heating said sample at about 100 degrees C for about 5 minutes;

(c) adding alkali to said sample;

(d) heating at about 105 degrees C for about 5 to about 30 minutes;

(e) centrifuging said sample while still hot to isolate said nucleic acids in supernatant.

12. The method of claim 11 wherein the alkali is sodium hydroxide.

13. The method of claim 12 wherein the centrifugation is performed for about 2 minutes at about 14,000 rpm.

14. The method of claim 11 wherein the buffer of step (a) also contains a nonionic surfactant.

15. The method of claim 14 wherein the nonionic surfactant is Tween-20.

* * * * *

SEQUENCE LISTING

<160> NUMBER OF SEQ ID NOS: 10

<210> SEQ ID NO 1
<211> LENGTH: 24
<212> TYPE: DNA
<213> ORGANISM: HUMAN

<400> SEQUENCE: 1
tataaacttg tggtagttgg acct                 24

<210> SEQ ID NO 2
<211> LENGTH: 20
<212> TYPE: DNA
<213> ORGANISM: HUMAN

<400> SEQUENCE: 2
cgtccacaaa atgattctga                      20

<210> SEQ ID NO 3
<211> LENGTH: 21
<212> TYPE: DNA
<213> ORGANISM: HUMAN

<400> SEQUENCE: 3
tcagcaaaga caagacagct a                    21

<210> SEQ ID NO 4
<211> LENGTH: 18
<212> TYPE: DNA

```
<213> ORGANISM: HUMAN

<400> SEQUENCE: 4
agcaatgccc tctcaaga                                                        18

<210> SEQ ID NO 5
<211> LENGTH: 24
<212> TYPE: DNA
<213> ORGANISM: HUMAN

<400> SEQUENCE: 5
agtaaaaggt gcactgtaat aatc                                                 24

<210> SEQ ID NO 6
<211> LENGTH: 23
<212> TYPE: DNA
<213> ORGANISM: HUMAN

<400> SEQUENCE: 6
gtgtcgagaa tatccaagag cca                                                  23

<210> SEQ ID NO 7
<211> LENGTH: 28
<212> TYPE: DNA
<213> ORGANISM: HUMAN

<400> SEQUENCE: 7
gactgtgttt ctcccttctc aggattcc                                             28

<210> SEQ ID NO 8
<211> LENGTH: 28
<212> TYPE: DNA
<213> ORGANISM: HUMAN

<400> SEQUENCE: 8
tatcgtcaag gcactcttgc ctacgcca                                             28

<210> SEQ ID NO 9
<211> LENGTH: 34
<212> TYPE: DNA
<213> ORGANISM: HUMAN

<400> SEQUENCE: 9
gacataacag ttatgatttt gcagaaaaca gatc                                      34

<210> SEQ ID NO 10
<211> LENGTH: 26
<212> TYPE: DNA
<213> ORGANISM: HUMAN

<400> SEQUENCE: 10
ttagtagtag aaggacgacg atggcg                                               26
```